United States Patent
Carlson et al.

(10) Patent No.: US 9,427,342 B2
(45) Date of Patent: *Aug. 30, 2016

(54) WOVEN FABRIC WITH SHAPE MEMORY ELEMENT STRANDS

(71) Applicant: Cook Medical Technologies LLC, Bloomington, IN (US)

(72) Inventors: James M. Carlson, Warsaw, IN (US); Shyam S. V. Kuppurathanam, Bloomington, IN (US); Fred T. Parker, Unionville, IN (US); Rebecca Sue Todd, Solsberry, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/577,777

(22) Filed: Dec. 19, 2014

(65) Prior Publication Data

US 2015/0127088 A1 May 7, 2015

Related U.S. Application Data

(60) Continuation of application No. 13/453,630, filed on Apr. 23, 2012, now Pat. No. 8,940,041, which is a division of application No. 12/045,351, filed on Mar. 10, 2008, now Pat. No. 8,177,834.

(60) Provisional application No. 60/906,412, filed on Mar. 12, 2007.

(51) Int. Cl.
*A61F 2/07* (2013.01)
*A61F 2/90* (2013.01)
(Continued)

(52) U.S. Cl.
CPC . *A61F 2/90* (2013.01); *A61F 2/07* (2013.01); *A61L 31/022* (2013.01); *A61L 31/041* (2013.01); *A61L 31/14* (2013.01); *D02G 3/12* (2013.01); *D02G 3/448* (2013.01); *D03D 3/02* (2013.01); *D03D 13/004* (2013.01); *D03D 13/008* (2013.01); *D03D 15/00* (2013.01); *D03D 15/08* (2013.01); *A61F 2/06* (2013.01); *A61F 2002/075* (2013.01); *A61F 2210/0014* (2013.01);
(Continued)

(58) Field of Classification Search
CPC ............. A61F 2/04; A61F 2/06; A61F 2/07; A61F 2/90; A61F 2210/0014; A61F 2013/00238; D02G 3/448; D03D 13/004; D03D 13/008; D03D 15/00; D03D 15/08
USPC ............... 442/1–6, 181–189; 623/1.19, 1.53
See application file for complete search history.

(56) References Cited

U.S. PATENT DOCUMENTS 3,095,017 A 6/1963 Bleiler et al.
3,108,357 A 10/1963 Liebig
(Continued)

OTHER PUBLICATIONS

PCT International Search Report for PCT/US2008/003251, dated Apr. 22, 2009, 3 pgs.
(Continued)

*Primary Examiner* — David Isabella
*Assistant Examiner* — Dinah Baria
(74) *Attorney, Agent, or Firm* — Brinks Gilson & Lione

(57) ABSTRACT

The disclosure relates to a woven fabric for use in an implantable medical device. The woven fabric comprises shape memory element strands woven with textile strands. At least one of the shape memory element strands has at least one float of at least five textile strands between binding points.

14 Claims, 5 Drawing Sheets

(51) Int. Cl.
*A61L 31/02* (2006.01)
*A61L 31/04* (2006.01)
*A61L 31/14* (2006.01)
*D02G 3/12* (2006.01)
*D02G 3/44* (2006.01)
*D03D 3/02* (2006.01)
*D03D 13/00* (2006.01)
*D03D 15/00* (2006.01)
*D03D 15/08* (2006.01)
*A61F 2/06* (2013.01)

(52) U.S. Cl.
CPC ........ *A61L2400/16* (2013.01); *C08L 2201/12* (2013.01); *D10B 2101/20* (2013.01); *D10B 2321/021* (2013.01); *D10B 2321/022* (2013.01); *D10B 2321/042* (2013.01); *D10B 2331/04* (2013.01); *D10B 2331/10* (2013.01); *D10B 2401/046* (2013.01); *D10B 2401/061* (2013.01); *D10B 2509/06* (2013.01)

(56) References Cited

U.S. PATENT DOCUMENTS

| | | | |
|---|---|---|---|
| 3,304,557 A | 2/1967 | Polansky | |
| 3,582,444 A | 6/1971 | Ngo et al. | |
| 4,340,091 A | 7/1982 | Skelton et al. | |
| 4,517,687 A | 5/1985 | Liebig et al. | |
| 4,530,113 A | 7/1985 | Matterson | |
| 4,610,688 A | 9/1986 | Silvestrini et al. | |
| 4,652,263 A | 3/1987 | Herweck et al. | |
| 4,670,286 A | 6/1987 | Nyilas et al. | |
| 4,792,336 A | 12/1988 | Hiavacek et al. | |
| 4,816,028 A | 3/1989 | Kapadia et al. | |
| 4,834,755 A | 5/1989 | Silvestrini et al. | |
| 4,892,539 A | 1/1990 | Koch | |
| 5,178,630 A | 1/1993 | Schmitt | |
| 5,197,977 A | 3/1993 | Hoffman, Jr. et al. | |
| 5,217,493 A | 6/1993 | Read et al. | |
| 5,282,848 A | 2/1994 | Schmitt | |
| 5,366,504 A | 11/1994 | Anderson et al. | |
| 5,370,682 A | 12/1994 | Schmitt | |
| 5,385,580 A | 1/1995 | Schmitt | |
| 5,487,858 A | 1/1996 | Schmitt | |
| 5,496,364 A | 3/1996 | Schmitt | |
| 5,509,931 A | 4/1996 | Schmitt | |
| 5,599,321 A | 2/1997 | Conway et al. | |
| 5,653,746 A | 8/1997 | Schmitt | |
| 5,674,276 A | 10/1997 | Andersen et al. | |
| 5,697,970 A | 12/1997 | Schmitt et al. | |
| 5,733,327 A | 3/1998 | Igaki et al. | |
| 5,800,514 A | 9/1998 | Nunez et al. | |
| 5,824,037 A | 10/1998 | Fogarty et al. | |
| 5,843,158 A | 12/1998 | Lenker et al. | |
| 5,891,191 A | 4/1999 | Stinson | |
| 5,976,179 A | 11/1999 | Inoue | |
| 6,045,568 A | 4/2000 | Igaki et al. | |
| 6,080,177 A | 6/2000 | Igaki et al. | |
| 6,136,022 A | 10/2000 | Nunez et al. | |
| 6,159,239 A | 12/2000 | Greenhalgh | |
| 6,161,399 A | 12/2000 | Jayaraman | |
| 6,164,339 A | 12/2000 | Greenhalgh | |
| 6,200,335 B1 | 3/2001 | Igaki | |
| 6,221,099 B1 | 4/2001 | Andersen et al. | |
| 6,346,492 B1 | 2/2002 | Koyfman | |
| 6,387,122 B1 | 5/2002 | Cragg | |
| 6,395,021 B1 | 5/2002 | Hart et al. | |
| 6,485,524 B2 | 11/2002 | Strecker | |
| 6,494,907 B1 | 12/2002 | Bulver | |
| 6,540,773 B2 | 4/2003 | Doug | |
| 6,547,820 B1 | 4/2003 | Staudenmeier | |
| 6,581,366 B1 | 6/2003 | Andrews | |
| 6,663,667 B2 | 12/2003 | Dehdashtian et al. | |
| 6,685,736 B1 | 2/2004 | White et al. | |
| 6,792,979 B2 | 9/2004 | Konya et al. | |
| 6,805,706 B2 | 10/2004 | Solovay et al. | |
| 6,814,754 B2 | 11/2004 | Greenhalgh | |
| 6,849,088 B2 | 2/2005 | Dehdashtian et al. | |
| 6,881,221 B2 | 4/2005 | Golds | |
| 7,063,721 B2 | 6/2006 | Takahashi et al. | |
| 7,122,052 B2 | 10/2006 | Greenhalgh | |
| 7,185,597 B1 | 3/2007 | Phillips et al. | |
| 7,338,531 B2 | 3/2008 | Ellis et al. | |
| 7,530,996 B2 | 5/2009 | Bentele et al. | |
| 7,651,522 B2 | 1/2010 | Busch et al. | |
| 7,670,367 B1 | 3/2010 | Chouinard et al. | |
| 7,699,887 B2 | 4/2010 | Burnside et al. | |
| 2001/0021870 A1 | 9/2001 | Edwin et al. | |
| 2001/0047198 A1 | 11/2001 | Drasler et al. | |
| 2001/0056299 A1 | 12/2001 | Thompson | |
| 2002/0034902 A1 | 3/2002 | Litton | |
| 2002/0042644 A1 | 4/2002 | Greenhalgh | |
| 2002/0052649 A1 | 5/2002 | Greenhalgh | |
| 2002/0156522 A1 | 10/2002 | Ivancey et al. | |
| 2003/0204235 A1 | 10/2003 | Edens et al. | |
| 2003/0229389 A1 | 12/2003 | Escano | |
| 2004/0209538 A1 | 10/2004 | Klinge et al. | |
| 2004/0215320 A1 | 10/2004 | Machek | |
| 2005/0008763 A1 | 1/2005 | Schachter | |
| 2005/0149173 A1 | 7/2005 | Hunter et al. | |
| 2005/0154444 A1 | 7/2005 | Quadri | |
| 2005/0154446 A1 | 7/2005 | Phillips et al. | |
| 2005/0163954 A1 | 7/2005 | Shaw | |
| 2005/0187604 A1 | 8/2005 | Eells et al. | |
| 2005/0240261 A1 | 10/2005 | Rakos et al. | |
| 2005/0283224 A1 | 12/2005 | King | |
| 2005/0288797 A1 | 12/2005 | Howland | |
| 2006/0009839 A1 | 1/2006 | Tan | |
| 2006/0019561 A1 | 1/2006 | Schindzielorz et al. | |
| 2006/0142840 A1 | 6/2006 | Sherry et al. | |
| 2006/0281382 A1* | 12/2006 | Karayianni et al. | 442/181 |
| 2006/0293749 A1 | 12/2006 | Hudgins et al. | |
| 2007/0207186 A1 | 9/2007 | Scanlon et al. | |
| 2007/0224238 A1 | 9/2007 | Mansmann et al. | |
| 2007/0270742 A1 | 11/2007 | Guetty | |
| 2008/0228028 A1 | 9/2008 | Carlson et al. | |
| 2009/0171435 A1 | 7/2009 | Kuppurathanam et al. | |
| 2009/0171443 A1 | 7/2009 | Kuppurathanam et al. | |
| 2009/0171451 A1 | 7/2009 | Kuppurathanam et al. | |
| 2009/0192597 A1 | 7/2009 | Bentele et al. | |
| 2009/0264934 A1 | 10/2009 | Youssef et al. | |
| 2009/0299408 A1 | 12/2009 | Schuldt-Hempe et al. | |
| 2010/0063576 A1 | 3/2010 | Schaeffer et al. | |
| 2010/0074934 A1 | 3/2010 | Hunter | |

OTHER PUBLICATIONS

PCT Written Opinion for PCT/Us2008/003251, dated Sep. 12, 2009, 6 pgs.
Office Action for corresponding U.S. Appl. No. 13/453,630 dated Sep. 9, 2013, 9 pages.
Response to Non-Final Office Action filed in corresponding U.S. Appl. No. 13/453,630 dated Dec. 9, 2013, 11 pages.
Final Office Action for corresponding U.S. Appl. No. 13/453,630 dated Mar. 7, 2014, 11 pages.
Response to Final Office Action filed in corresponding U.S. Appl. No. 13/453,630 dated May 7, 2014, 9 pages.
Advisory Action for corresponding U.S. Appl. No. 13/453,630 dated May 22, 2014, 3 pages.
Pre-Appeal Brief filed in corresponding U.S. Appl. No. 13/453,630 dated Aug. 7, 2014, 6 pages.
Pre-Brief Appeal Conference Decision for corresponding U.S. Appl. No. 13/453,630 dated Sep. 5, 2014, 2 pages.
Notice of Allowance for corresponding U.S. Appl. No. 13/453,630 dated Sep. 15, 2014, 7 pages.

* cited by examiner

WOVEN FABRIC WITH SHAPE MEMORY ELEMENT STRANDS

PRIORITY CLAIM

This application is a continuation of U.S. patent application Ser. No. 13/453,630 filed Apr. 23, 2012, which is a divisional of U.S. patent application Ser. No. 12/045,351 filed Mar. 10, 2008 which claims the benefit of provisional U.S. Patent Application Ser. No. 60/906,412, filed Mar. 12, 2007, which are incorporated herein by reference in their entirety.

TECHNICAL FIELD

The present invention relates to woven fabrics. More particularly, the present invention relates to woven fabrics for implantable medical devices.

BACKGROUND OF THE INVENTION

Aneurysms occur in blood vessels in locations where, due to age, disease or genetic predisposition, insufficient blood vessel strength or resiliency may cause the blood vessel wall to weaken and/or lose its shape as blood flows it, resulting in a ballooning or stretching of the blood vessel at the limited strength/resiliency location, thus forming an aneurysmal sac. Left untreated, the blood vessel wall may continue to expand to the point where the remaining strength of the blood vessel wall cannot hold and the blood vessel will fail at the aneurysm location, often with fatal result.

To prevent rupture of an aneurysm, a stent graft of a tubular construction may be introduced into the blood vessel and deployed and secured in a location within the blood vessel such that the stent graft spans the aneurysmal sac. The outer surface of the stent graft, at its opposed ends, abuts and seals against the interior wall of the blood vessel at a location where the blood vessel wall has not suffered a loss of strength or resiliency. The stent graft channels the blood flow through the hollow interior of the stent graft, thereby reducing, if not eliminating, any stress on the blood vessel wall at the aneurysmal sac location.

Stent grafts are typically configured by separately forming the graft and the stent(s), and then attaching the graft to stent(s). To attach a stent to a graft, the graft is typically inserted into, or pulled over, the stent, and the graft is sewn to the structural components of the stent. Alternatively, the stent may be formed on the graft such that the individual wires of the stent are threaded through specially provided projecting fabric loops on the surface of the graft, thereby creating attachment of the graft to the stent.

Attachment of the graft to the stent in these ways may result in an unneeded bulk. For example, the size of the stent graft, including the wire cage of the stent and the fabric of the graft, as well as the bulk of the connection mechanisms between them, limits the ultimate size of a stent graft that can be made that still fits within a catheter for smaller blood vessel diameter locations. Additionally, known mechanisms for attachment of the graft to the stent may provide potential sites for separation between the graft and stent. For example, during manufacture, handling or delivery of the stent graft, the attachment mechanisms may tear or fail, allowing the graft to partially or fully separate from the stent. Furthermore, attachment sites of the stent to graft may permit undesirable leakage of body fluids through the graft structure. For example, stents sutured to grafts may create interstices at the site of suture, increasing the grafts' porosity.

SUMMARY

In one example, the woven fabric comprises shape memory element strands and textile strands aligned in a first direction and textile strands aligned in a second direction. At lease one of the shape memory element strands has at least one float of at least five textile strands aligned in the second direction. Preferably, the textile strands comprise polyester and the shape memory element strands comprise superelastic nitinol wire.

In another example, a method for producing woven fabric is provided. The method comprises aligning textile strands and shape memory element strands in a first direction, aligning textile strands in a second direction, and weaving the shape memory element strands and textile strands to produce a fabric. At least one of the shape memory element strands has at least one float of at least five textile strands in the second direction. Preferably, the weave is a tubular double weave. Even more preferably, the shape memory element strands comprise superelastic nitinol wires that are heated on a mandrel and cooled prior to weaving.

Other systems, methods, features and advantages will be, or will become, apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The woven fabric may be better understood with reference to the following drawings and description. The components in the figures are not necessarily to scale, emphasis instead being placed upon illustrating the principles of the disclosure. Moreover, in the figures, like referenced numerals designate corresponding parts throughout the different views.

DETAILED DESCRIPTION

Figure 1A:
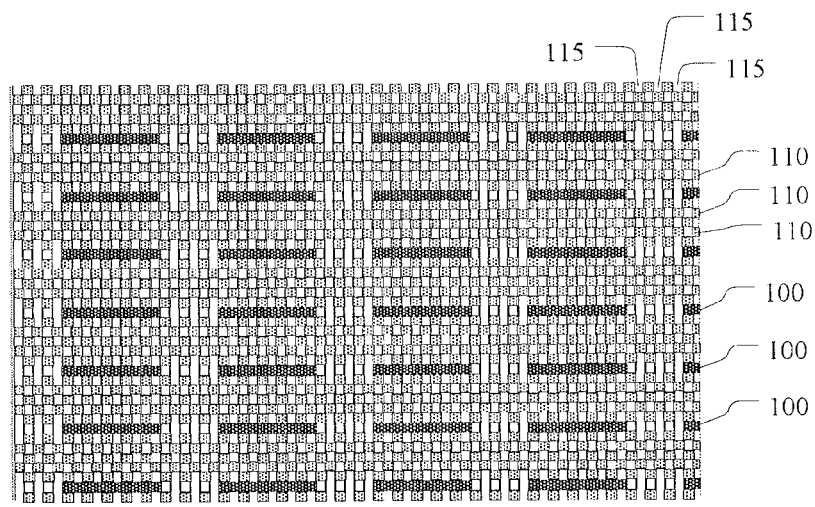
FIGS. 1A and 1B are a schematic representation of one example of woven fabric weave pattern.

The present disclosure relates to a fabric comprising shape memory element strands and textile strands aligned in a first direction woven with textile strands aligned in a second direction such that the shape memory element strands have floats of multiple textile strands.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present disclosure. All publications, patent applications, patents and other references mentioned herein are incorporated by reference in their entirety. The materials, methods, and examples disclosed herein are illustrative only and not intended to be limiting.

Definitions

The term "implantable" refers to an ability of a medical device to be positioned at a location within a body, such as within a body lumen.

The term "strand" as used herein is a generic term for a continuous strand of material suitable for weaving. For example, strands may include, but are not limited to monofilaments, filaments twisted together, fibers spun together or otherwise joined, yarns, roving yarns, crepe yarns, ply yarns, cord yarns, threads, strings, filaments laid together without twist, as well as other configurations.

The term "binding point" refers to the intersection of a single strand in a first direction with strands in a second direction. For example, a strand in a first direction may run "over" one or multiple strands in a second direction, have a binding point, and run "under" one or more subsequent strands in the second direction.

The term "float" refers to that portion of a strand in a first direction that extends over or under two or more strands in a second direction without a binding point. For example, a strand in a first direction may have a binding point with strands in a second direction, then float over 5 adjacent strands in the second direction, then have another binding point with strands in the second direction.

The term "alloy" refers to a substance composed of two or more metals or of a metal and a nonmetal intimately united, such as by chemical or mechanical interaction. Alloys can be formed by various methods, including being fused together and dissolving in each other when molten, although molten processing is not a requirement for a material to be within the scope of the term "alloy."

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing."Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

The term "prosthesis" means any replacement for a body part or for a function of that body part; or any device that enhances or adds functionality to a physiological system.

The term "endoluminal" describes objects that are found or can be placed inside a lumen or space in the human or animal body. This includes lumens such as blood vessels, parts of the gastrointestinal tract, ducts such as bile ducts, parts of the respiratory system, etc. "Endoluminal prosthesis" thus describes a prosthesis that can be placed inside one of these lumens. The term "about" used with reference to a quantity includes variations in the recited quantity that are equivalent to the quantity recited, such as an amount that is insubstantially different from a recited quantity for an intended purpose or function.

Weave

The woven fabric may comprise any kind of weave as a primary weave. For example, the woven fabric primary weave may include, but is not limited to, weaves such as plain weaves, basket weaves, rep or rib weaves, twill weaves (e.g., straight twill, reverse twill, herringbone twill), satin weaves, and double weaves (e.g., double-width, tubular double weave, reversed double weave). In one example, the primary weave comprises a tubular double layer weave.

Determination of which primary weave is most appropriate may be based on a variety of factors, including intended clinical application, desired properties of the woven fabric, weave type, and strand properties such as the size or denier of the strand and the shape of the strands. For example, for percutaneous application, thin fabrics are desired. Such thin fabrics comprise strands having a low denier. In one example, textile strands in the woven fabric range in size from about 0.1 denier to about 200 denier.

FIG. 1A illustrates one example of a woven fabric with shape memory element strands 100 and textile strands 110 in a first direction and textile strands 115 in a second direction. Textile strands 110 and 115 are woven in a primary plain weave characterized by the regular interlacement of textile strands 110 and 115 in a 1/1 order. That is, each textile strand 110 moves alternatively over and under adjacent textile strands 115. This plain weave produces the maximum number of binding points, and is thus a firm, durable primary weave.

For certain clinical applications, endoluminal prostheses comprising woven fabrics having low porosity and low permeability are particularly preferred. For example, woven fabrics and endoluminal prostheses that comprise woven fabrics with integrated shape memory element strands having minimal interlacement may provide decreased porosity as compared to traditional stent-graft structures. Traditional stent grafts are configured by suturing the stent to the graft. Attachment of the stent to the graft in this manner may result in undesirable leakage of body fluids through the attachment sites of the stent to the graft. For example, stents sutured to grafts may create interstices at the site of suture, increasing the grafts' porosity.

Figure 1B:
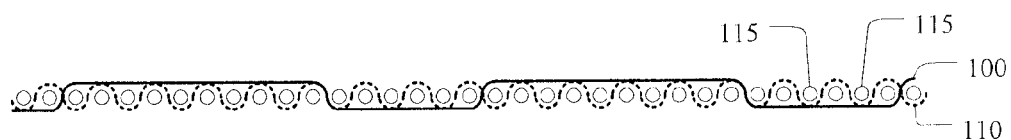

In one aspect, shape memory element strands 100 woven with a high proportion of floats to binding points may decrease the fabric porosity by minimizing the interlacement of shape memory element strands 100 with textile strands 115. The shape memory element strands 100 have an over-10/under-6 interlacement configuration, shown in FIG. 1B. That is, the shape memory element strands 100 float "over" ten textile strands 115 and then cross "under" six textile strands 115. The terms "over" and "under" are meant to be relative. For example, the inverse is also true; shape memory element strands 100 float "under" ten textile strands 115 and then cross "over" six textile strands 115. This minimal interlacement with textile strands 115 permits the woven fabric to maintain low porosity by reducing the number of binding points while simultaneously providing the fabric with shape memory characteristics. Additionally, spacing shape memory element strands 100 every sixth strand in the first direction improves the fabric's low porosity by further reducing shape memory element strand binding points while allowing the fabric to maintain desirable shape memory characteristics.

Figure 2:
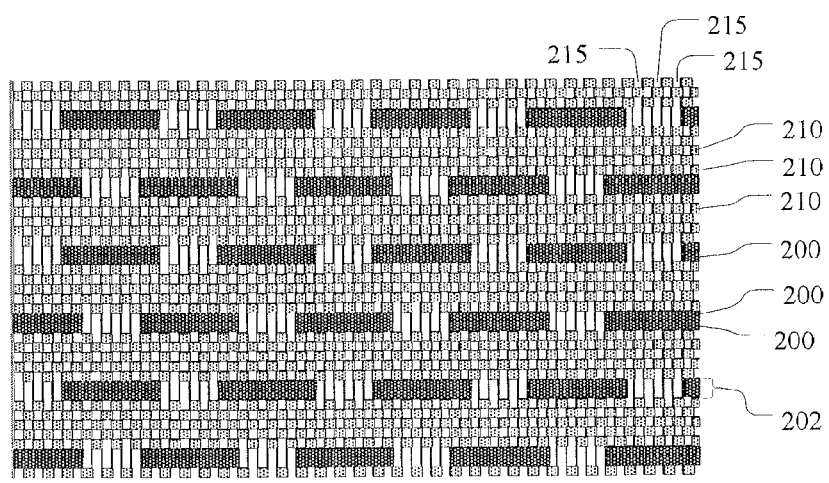
FIG. 2 is a schematic representation of another example of woven fabric weave pattern.

Alternative examples may have shape memory element strands located adjacent one another or have offset binding points to improve the woven fabric's low porosity and shape memory characteristics. For example, FIG. 2 illustrates woven fabric with shape memory element strands 200 and textile strands 210 in a first direction and textile strands 215 in a second direction. Similar to FIG. 1B, textile strands 210 and 215 are woven in a plain weave and shape memory element strands 200 have an over-10/under-6 interlacement configuration.

Shape memory element strands 200 are woven with two shape memory element strands 202 adjacent one another. Adjacent shape memory element strands 202 may provide the woven fabric with superior shape memory characteristics in the area surrounding adjacent shape memory element strands 202. The binding points of shape memory element strands 200 occur in a diagonal progression across the fabric, moving systematically across seven textile strands 215. This may serve to distribute shape memory binding points across several different textile strands 115 and further reduce fabric porosity.

Figure 3A:
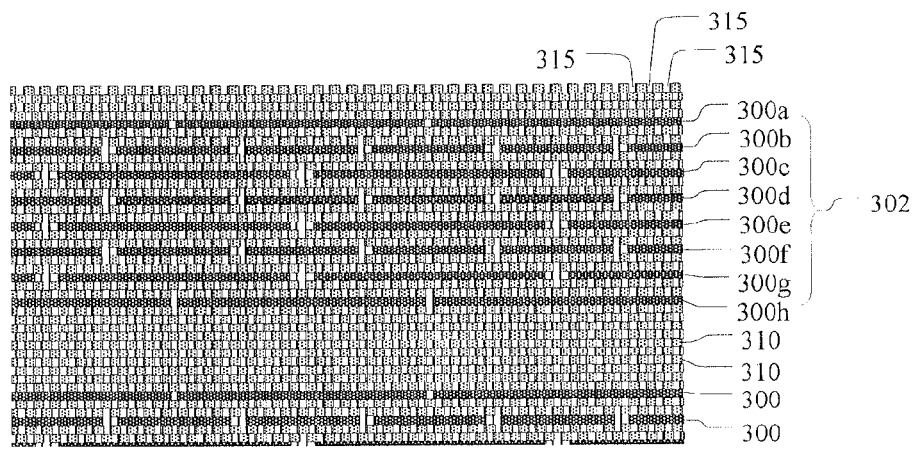
FIGS. 3A, 3B, 3C, and 3D are schematic representations of a further example of woven fabric weave pattern.
Figure 3B:
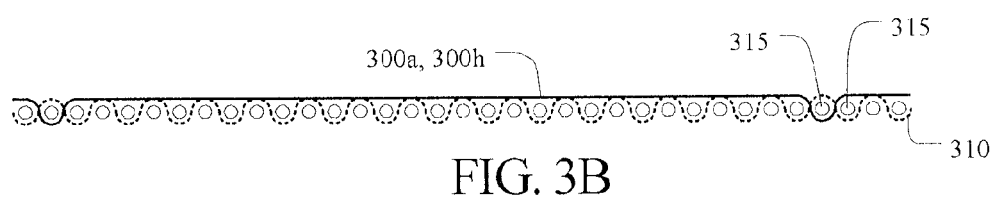
Figure 3C:
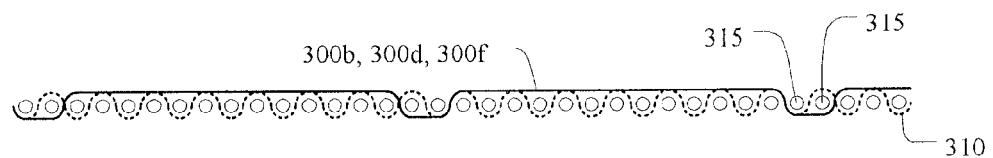
Figure 3D:
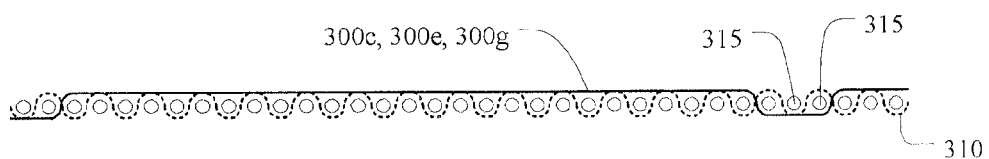

FIG. 3A depicts a further example of a woven fabric comprising shape memory element strands 300 and textile strands 310 in a first direction and textile strands 315 in a second direction. Shape memory element strands 300 are arranged into series 302 comprising eight shape memory element strands 300a-300h. Each series 302 comprises varying floats and interlacement configurations as well as differing binding points. For example, 1) the proximal and distal shape memory element strands 300a and 300h of series 302 have an over-29/under-1 configuration, shown in FIG. 3B; 2) FIG. 3C illustrates intermediate shape memory strands 300b, 300d, 300f of series 302 having an over-13/under-2 configuration; and 3) FIG. 3D shows intermediate shape memory strands 300c, 300e, 300g of series 302 having an over-27/under-3 configuration. The lengthy floats of shape memory element strands 300 permit the woven fabric to maintain an extremely low porosity by reducing the binding points. Organizing shape memory element strands 300 into series 302 provides the fabric with desirable shape memory characteristics while distributing stress across textile strands 310 and 315.

Figure 4:
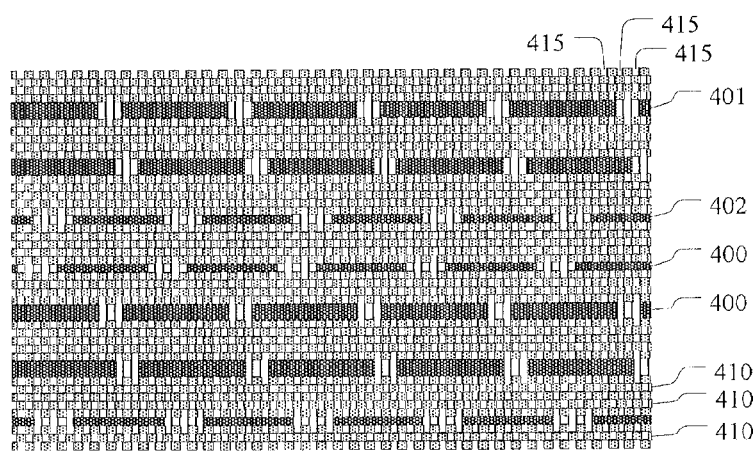
FIG. 4 is a schematic representation of yet another woven fabric weave pattern.
Figure 5A:
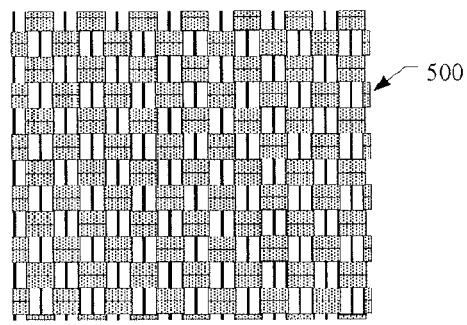
FIGS. 5A, 5B, 5C, and 5D are schematic representations of textile strands weave patterns.
Figure 5B:
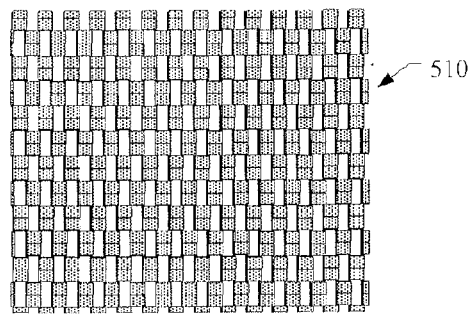
Figure 5C:
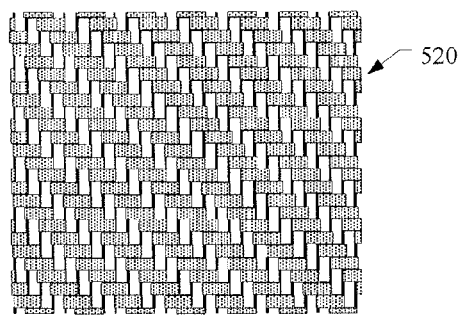
Figure 5D:
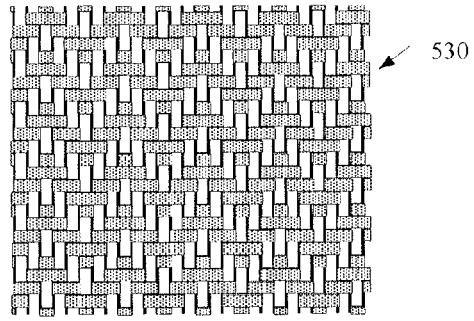

Further examples may have shape memory element strands of varying sizes as compared to textile strands or other shape memory element strands. For example, FIG. 4 illustrates a woven fabric with shape memory element strands 400 and textile strands 410 in a first direction and textile strands 415 in a second direction. Shape memory element strands 401 have a larger size than shape memory element strands 402 and textile strands 410 and 415. Shape memory element strands of increased size may permit the use of fewer shape memory element strands and allow for fewer binding points between textile strands and shape memory element strands.

Although the woven fabrics in the illustrative figures are shown with textile strands having a primary weave comprising a plain weave, the textile strands may have any suitable primary weave. The specific primary weave will depend on several factors, including the interlacement pattern of shape memory element strands, type of application, properties of the woven fabric that are desired, and strand properties such as denier. For example, FIGS. 5A-5D illustrate textile strands having a primary weave comprising a basket weave 500, a rep weave 510, a twill weave 520, and a herringbone weave 530.

Textile Strands

The textile strands may comprise any biocompatible material. The textile strands may be natural, synthetic, or manufactured. For example, biocompatible materials from which textile strands can be formed include, but are not limited to, polyesters, such as poly(ethylene terephthalate); fluorinated polymers, such as polytetrafluoroethylene (PTFE) and fibers of expanded PTFE; and polyurethanes. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any fibrous material may be used to form a textile strand material, provided the final textile is biocompatible.

Polymers that can be formed into fibers for making textile strands are particularly preferred. For example, suitable polymers include polyethylene, polypropylene, polyaramids, polyacrylonitrile, nylons and cellulose, in addition to polyesters, fluorinated polymers, and polyurethanes as listed above. Desirably, textile strands comprise biocompatible polyesters. Even more desirable, textile strands comprise polyethylene terephthalate and PTFE. A preferred commercial example of polyethylene terephthalate especially suited for weaving is Dacron®. These materials are inexpensive, easy to handle, have good physical characterstics and are suitable for clinical application.

Shape Memory Element Strands

Materials used for the shape memory element strands need only be biocompatible or able to be made biocompatible. Suitable materials for the shape memory element strands include shape memory metals and shape memory polymers.

Suitable shape memory metals include, for example, TiNi (Nitinol), CuZnAl, and FeNiAl alloys. Particularly preferred are "superelastic" metal alloys. Superelasticity refers to a shape memory metal alloy's ability to spring back to its austenitic form from a stress-induced martensite at temperatures above austenite finish temperature. The austenite finish temperature refers to the temperature at which the transformation of a shape memory metal from the martensitic phase to the austenitic phase completes.

For example, martensite in a nitinol alloy may be stress induced if stress is applied at a temperature above the nitinol alloy's austenite start temperature. Since austenite is the stable phase at temperatures above austenite finish temperature under no-load conditions, the material springs back to its original shape when the stress is removed. This extraordinary elasticity is called superelasticity. In one example, nitinol wire may be in the superelastic condition where the wire has been cold worked at least 40% and given an aging heat treatment at approximately 500 degrees Celsius for at least 10 minutes. The nitinol wire is in its fully superelastic condition where the use temperature is greater than the austenite finish temperature of the nitinol wire.

Suitable shape memory polymers include, without limitation, polyethers, polyether esters, polyether amides, polyacrylates, polyamides, polysiloxanes, polyurethanes, polyurethane-ureas, and urethane-butadiene copolymers. See, for example, U.S. Pat. No. 6,720,402 to Langer et al.; U.S.

Pat. No. 5,506,300 to Ward et al.; U.S. Pat. No. 5,145,935 to Hayashi; and U.S. Pat. No. 5,665,822 to Bitler et al.

Medical Devices

The fabric of the present invention is suitable for use in a variety of implantable or insertable medical devices, for example surgically or endoluminally, of any shape or configuration comprising woven fabric. Typical subjects (also referred to herein as "patients") are vertebrate subjects (i.e., members of the subphylum cordata), including, mammals such as cattle, sheep, pigs, goats, horses, dogs, cats and humans.

Typical sites for placement of the medical devices include the coronary and peripheral vasculature (collectively referred to herein as the vasculature), heart, esophagus, trachea, colon, gastrointestinal tract, biliary tract, urinary tract, bladder, prostate, brain and surgical sites.

The medical device may be any device that is introduced temporarily or permanently into the body for the prophylaxis or therapy of a medical condition. For example, such medical devices may include, but are not limited to: endovascular grafts, stent grafts, balloon catheters, meshes, vascular grafts, stent-graft composites, filters (e.g., vena cava filters), vascular implants, tissue scaffolds, myocardial plugs, valves (e.g., venous valves), various types of dressings, endoluminal prostheses, vascular supports, or other known biocompatible devices.

One example of the present invention contemplates a tubular implantable prosthesis. Examples of prostheses that may require a tubular design include intraluminal prostheses, endovascular grafts, and radially deformable support components, such as radially deformable stents. Preferably, a medical device comprising the woven fabric comprises an endoluminal prosthesis.

Figure 6:
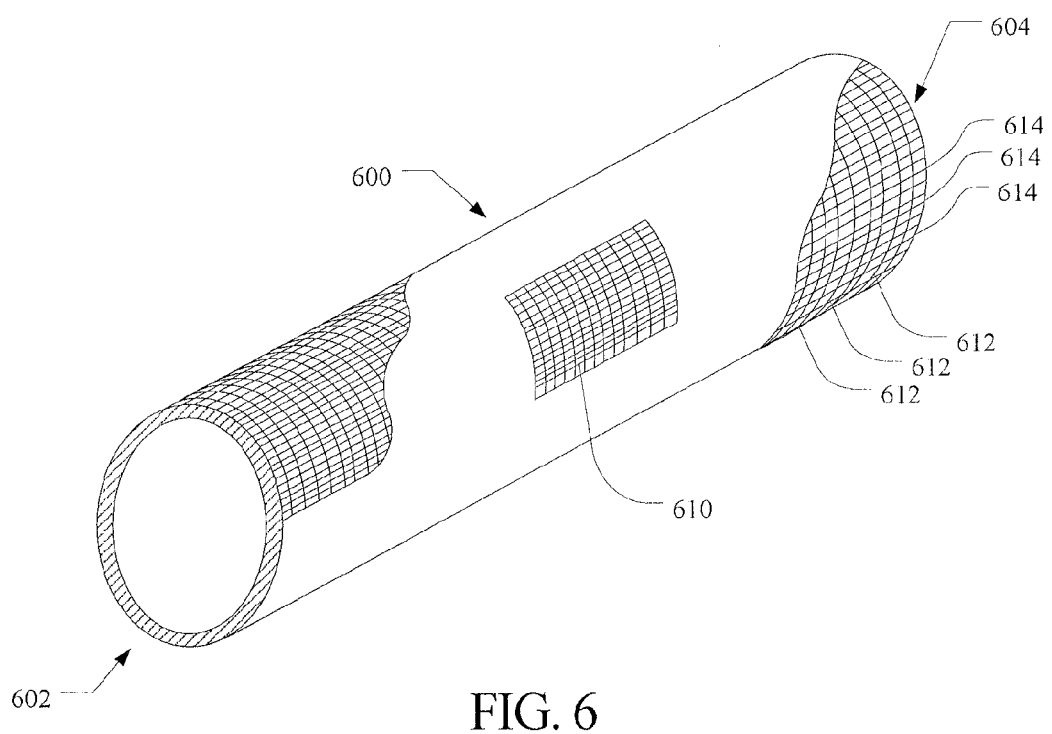
FIG. 6 is a perspective illustration of one example of a medical device comprising a woven fabric of the present invention.
Figure 7:
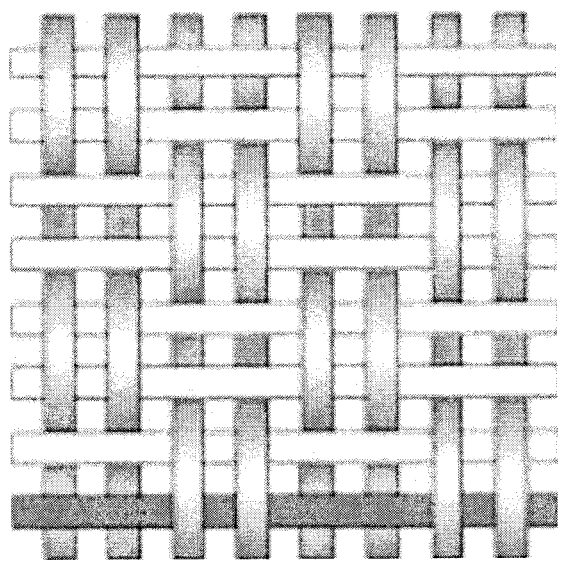
FIG. 7 shows a leno weave.
Figure 8:
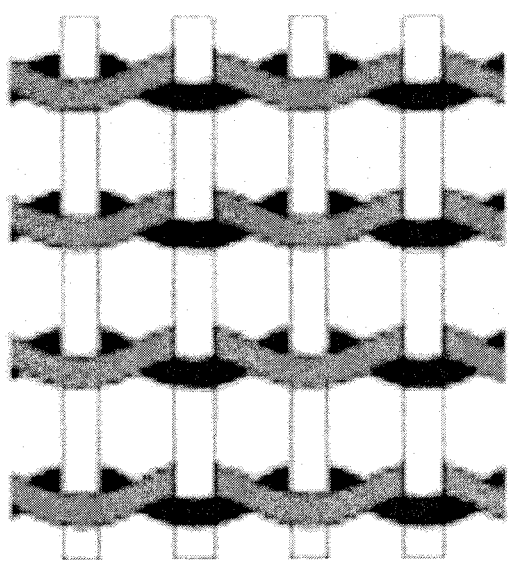
FIG. 8 shows a mock leno weave.

For example, FIG. 6 depicts an integrated tubular stent-graft 600 comprising a woven fabric 610. The woven fabric 610 has radial strands 612 and longitudinal strands 614, though the strands need not be radial and longitudinal and may have any suitable orientation. The radial strands 612 and longitudinal strands 614 may have any suitable weave configuration. For example, the radial strands 612 may comprise shape memory element strands 100 and textile strands 110 and the longitudinal strands 614 may comprise textile strands 115. Alternatively, the radial strands 612 of the woven fabric 610 may comprise shape memory element strands 300 and textile strands 310 and the longitudinal strands 614 may comprise textile strands 315. Series 302 of shape memory element strands 300 may be located about the proximal integrated stent-graft end 602 and distal integrated stent-graft end 604 to assist in sealing against a body vessel wall upon implantation.

The medical device may be balloon-expandable or, preferably, self-expanding and may be a bifurcated integrated stent-graft, an integrated stent-graft configured for any blood vessel including coronary arteries and peripheral arteries (e.g., renal, superficial femoral, carotid, and the like), a urethral integrated stent-graft, a biliary integrated stent-graft, a tracheal integrated stent-graft, a gastrointestinal integrated stent-graft, or an esophageal integrated stent-graft, for example.

Method of Manufacture

The present invention is also applicable to methods of producing a woven fabric comprising shape memory element strands and textile strands. In one embodiment, the method comprises providing textile strands and shape memory element strands, and weaving the shape memory element strands with the textile strands to produce a woven fabric.

The fabric may be woven in any way known to one of skill in the art. For example, the fabric may be woven on a table loom, a floor loom, a jacquard loom, a counterbalance loom, a jack loom, or an upright loom. Desirably, the fabric is woven on a floor loom.

The fabric may have any configuration possible, but desirably has warp and weft strands. Warp strands preferably include textile strands. Weft strands preferably include shape memory element strands and textile strands. In one example, the textile strands range in size from micro denier to about 200 denier.

Prior to weaving, the shape memory element strands may be further prepared. For example, shape memory element strands comprising shape memory metals may be wound around a shaped mandrel and heated to a temperature, preferably above the shape memory metal's austenite finish temperature, to impart a shape memory effect. In one example, superelastic nitinol wire may be cold worked at least 40% and given an aging heat treatment at approximately 500 degrees Celsius for at least 10 minutes. Imparting a shape memory effect on the shape memory element strands permits a fabric woven with such strands to assume a shape corresponding to that of the mandrel.

The shape memory element strands may be cooled, preferably to room temperature or below room temperature, to improve the shape memory element strands' pliability during weaving. For example, shape memory element strands comprising shape memory metals may be cooled below martensite start temperature. The martensite start temperature is the temperature at which the martensitic phase begins to form.

Following weaving of the fabric, the fabric may be heated such that the shape memory element strands obtain the shape memory previously imparted. For example, shape memory element strands comprising shape memory metals maybe be heated above the metal's austenite start temperature, preferably above the metal's austenite finish temperature to obtain the metal's full superelastic effect.

While various aspects and examples have been described, it will be apparent to those of ordinary skill in the art that many more examples and implementations are possible within the scope of the invention. Accordingly, the invention is not to be restricted except in light of the attached claims and their equivalents.

We claim:

1. A biocompatible woven fabric suitable for an implantable medical device comprising shape memory element strands and textile strands aligned in a first direction interlaced with textile strands aligned in a second direction, where at least one of the shape memory element strands aligned in the first direction has at least one float over at least five textile strands aligned in the second direction and at least one float under at least five textile strands aligned in the second direction, wherein the biocompatible woven fabric is adapted to be placed in a vessel and has low porosity and low permeability.

2. The biocompatible woven fabric of claim 1, where the textile strands comprise a polymer selected from the group consisting of polyester, polypropylene, polyethylene, polyurethane, polytetrafluoroethylene, and combinations thereof.

3. The woven fabric of claim 1, where the textile strands have a denier between 0.1 denier to 200 denier.

4. The biocompatible woven fabric of claim 1, where the shape memory element strands are selected from the group consisting of a shape memory polymer, a shape memory metal, and combinations thereof.

5. The biocompatible woven fabric of claim 1, where the shape memory element strands comprise superelastic nitinol wire.

6. The biocompatible woven fabric of claim 5, where the superelastic nitinol wire has a diameter between 70 µm to 125 µm.

7. The biocompatible woven fabric of claim 1, where the shape memory element strands in the first direction have at least one float of between six to twelve textile strands in the second direction.

8. The biocompatible woven fabric of claim 1, where the fabric comprises a primary weave selected from the group consisting of a plain weave, a basket weave, a rep weave, a rib weave, a twill weave, a leno weave, a mock lena weave, a satin weave, a double weave, or a variation thereof.

9. The biocompatible woven fabric of claim 1, where the fabric comprises a tubular double weave.

10. The biocompatible woven fabric of claim 1, further comprising any two or more of the following:
   textile strands comprising a polymer selected from the group consisting of polyester, polypropylene, polyethylene, polyurethane, polyletrafluoroethylene, and combinations thereof;
   textile strands comprising a denier between 0.1 denier to 200 denier;
   shape memory element strands selected from the group consisting of a shape memory polymer, a shape memory metal, and combinations thereof;
   shape memory element strands comprising superelastic nitinol wire having a diameter between 70 µm to about 125 µm;
   shape memory element strands in the first direction having at least one float of between six to twelve textile strands in the second direction; and
   a primary weave selected from the group consisting of a plain weave, a basket weave, a rep weave, a rib weave, a twill weave, a leno weave, a mock lena weave, a satin weave, a double weave, or a variation thereof.

11. A biocompatible woven tubular stent-graft comprising shape memory element strands aligned in a first direction and polyester strands aligned in the first direction interlaced with textile strands aligned in a second direction; and
   a primary weave comprising a tubular double weave;
   where at least one of the shape memory element strands has at least one float over at least five textile strands aligned in the second direction and at least one float under at least five textile strands aligned in the second direction, wherein the biocompatible woven tubular stent graft is adapted to be placed in a vessel and has low porosity and low permeability.

12. The biocompatible woven tubular stent-graft of claim 11, the shape memory element strands comprising a superelastic nitinol wire having a diameter between 70 µm to 125 µm and the textile strands comprising polyester having a denier between microdenier to 200 denier.

13. A biocompatible woven fabric suitable for an implantable medical device comprising shape memory element strands and textile strands aligned in a first direction interlaced with textile strands aligned in a second direction, where at least one of the shape memory element strands aligned in the first direction has at least one float over at least five textile strands aligned in the second direction, and at least one float under at least five textile strands aligned in the second direction, wherein the biocompatible woven fabric is adapted to be placed in the vessel and has low porosity and low permeability, and wherein the shape memory element strands consist of superelastic nitinol.

14. The biocompatible woven fabric of claim 11, wherein some of shape memory strands are arranged radially in a series about the stent graft at at least one end of the stent graft such that the density of shape memory strands at the at least one end of the stent graft is greater than along a length of the stent graft.

* * * * *